US Patent Number: 4,991,602
Date of Patent: Feb. 12, 1991

Amplatz et al.

[54] FLEXIBLE GUIDE WIRE WITH SAFETY TIP

[75] Inventors: Curtis A. Amplatz, St. Paul; Stuart Lind, Minneapolis, both of Minn.

[73] Assignee: Flexmedics Corporation, Minneapolis, Minn.

[21] Appl. No.: 372,049

[22] Filed: Jun. 27, 1989

[51] Int. Cl.⁵ .............................................. A61B 5/00
[52] U.S. Cl. .................................... 128/772; 128/657; 604/164; 604/280
[58] Field of Search ................. 128/657, 772; 604/95, 604/164, 170, 280, 282

[56] References Cited

U.S. PATENT DOCUMENTS

| | | | |
|---|---|---|---|
| 2,118,631 | 5/1938 | Wappler | 128/657 |
| 3,521,620 | 7/1970 | Cook | 128/772 |
| 3,612,058 | 10/1971 | Ackerman | 128/772 |
| 3,973,556 | 8/1976 | Fleischhacker et al. | 128/772 |
| 4,003,369 | 1/1977 | Heilman et al. | 128/772 |
| 4,456,017 | 1/1984 | Miles | 128/772 |
| 4,548,206 | 10/1985 | Osborne | 128/772 |
| 4,579,127 | 4/1986 | Haacke | 128/772 |
| 4,619,274 | 10/1986 | Morrison | 128/772 |
| 4,925,445 | 5/1990 | Sakamoto et al. | 128/772 |

FOREIGN PATENT DOCUMENTS 1232814 2/1988 Canada .

*Primary Examiner*—Randall L. Green
*Assistant Examiner*—Randy Shay
*Attorney, Agent, or Firm*—James R. Haller; Gregory P. Kaihoi; Mary P. Bauman

[57] ABSTRACT

A guide useful for guiding a catheter within a blood vessel is formed of a single length of shape memory alloy. The guide has a central portion of uniform diameter and substantially identical tapered end portions each terminating in enlarged diameter portions defining smoothly rounded beads which function to reduce trauma to the lumen of a blood vessel.

5 Claims, 1 Drawing Sheet

FLEXIBLE GUIDE WIRE WITH SAFETY TIP

BACKGROUND OF THE INVENTION

Elongated, flexible guide wires are often used in medical procedures to gain access to specific inner areas of the body without major surgery. Guide wires may be passed into the body via peripheral blood vessels, the gastrointestinal tract, or the urinary tract, and when in place may be used to guide catheters and the like into place.

A common method used to insert catheters in the human body is the percutaneous Seldinger technique. According to this method, a hollow introducer needle is inserted into a desired blood vessel under topical anesthesia. After the needle is properly placed, which may be indicated by the passage of blood through the needle, a guide wire is passed through the needle and into the vessel. Once the guide wire is in place, the needle is retracted and a catheter is introduced over the wire, the guide wire being used to maneuver the catheter to the desired point in the cardiovascular system. This point may be close to the area of insertion into the vessel, such as where the guide is simply used to introduce a catheter for intravenous fluid supply, or it may be far removed from that area, as when the guide is used in angiocardiographic applications. Once the catheter is in place, the guide is removed and the next step of the medical procedure may proceed.

To facilitate threading a guide through a predetermined body channel such as an artery, the guide may include a generally flexible body portion which is resistant to kinking and a forward end portion of increased flexibility, the end portion terminating in a smoothly rounded tip. The body portion may include a core of stainless steel or other metal, the core being appropriately dimensioned in cross section to provide the desired degree of flexibility to the guide wire.

To provide greater flexibility to the guide at its forward end, and provide radio opaqueness, a flexible length of helically wound wire forming an elongated coil is often employed at the forward end of the guide wire for this purpose. In this situation, a small plug commonly is employed at the forward end of the coil to provide the guide with a smoothly rounded tip and to restrain separation of the coil from the remainder of the wire when the guide wire is withdrawn, the plug being welded (including soldering or brazing) to the forward end of the core wire or to the forward end of a safety wire lying along the core wire. However, the forward plug may separate from the core or safety wire, making it difficult to extract the plug and the wire coil from the blood vessel into which it had been introduced. Also, leading coil lengths can become snagged on the distal end of a needle. Another difficulty with external helical coils is that there are practical limits to the coil diameter which may preclude the practical use of such wires in pediatric care where smaller blood vessels are encountered. U.S Pat. No. 4,619,274 describes a guide unit with an external helical coil having a forward end of sufficiently attenuated diameter so that it may be used in smaller vessels, the desired diameter being laboriously obtained by welding together a series of coils of progressively smaller diameters into a single coil of sequentially decreased diameter.

Unfortunately, the attachment via weldments of safety wires or core wires to forwardly positioned buttons in guide wires of the type described is not particularly strong. Moreover, several manufacturing steps are required, driving up the cost of these devices. It appears that failure occurs generally in the weldment between the forward end of the safety wire or core wire and the metal plug or button at the forward end of the guide wire, and this problem is particularly severe when the core wire or safety wire is made of a shape memory alloy such as nitinol. It would be desirable to provide a flexible guide having a forward tip which is far more securely fastened to the body of the guide, and further to provide a flexible guide with a small diameter that avoids the expense and weakened weldment joints necessitated by forming a helical coil from a series of independent wires.

SUMMARY OF THE INVENTION

The instant invention provides an elongated flexible guide useful for guiding a catheter within a blood vessel and which is free of external helical coils. The guide comprises an elongated, flexible metal wire of shape memory alloy having a central portion of uniform diameter and identical linearly tapered end portions. Each end portion terminates in an integral, enlarged diameter portion of the wire to form a bead or ball to facilitate introduction into a blood vessel and to reduce trauma to the vessel. As described in more detail below, the guide desirably is formed from a single, generally cylindrical length of flexible metal wire by known centerless grinding techniques. This guide is formed of a shape memory alloy of which the nickel/titanium alloy known as nitinol is an example.

DETAILED DESCRIPTION OF THE PREFERRED EMBODIMENTS

Figure 1:
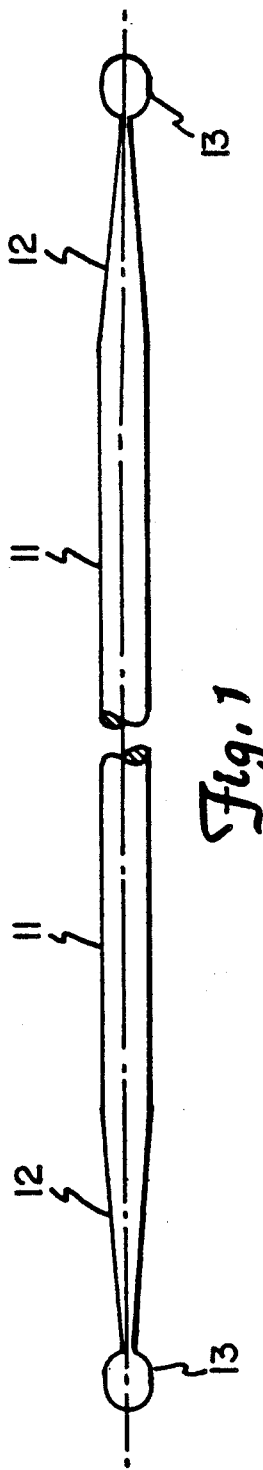
FIG. 1 is a broken-away side view of a guide in accordance with the present invention.
Figure 2:
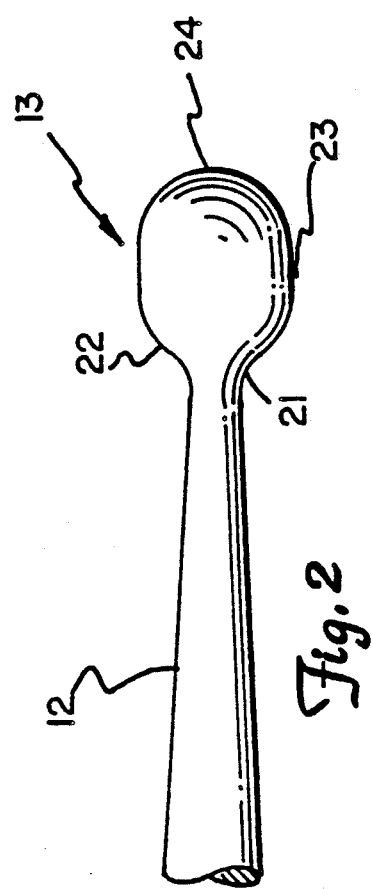
FIG. 2 is an enlarged view of the end portion of one embodiment of the guide shown in FIG. 1
Figure 3:
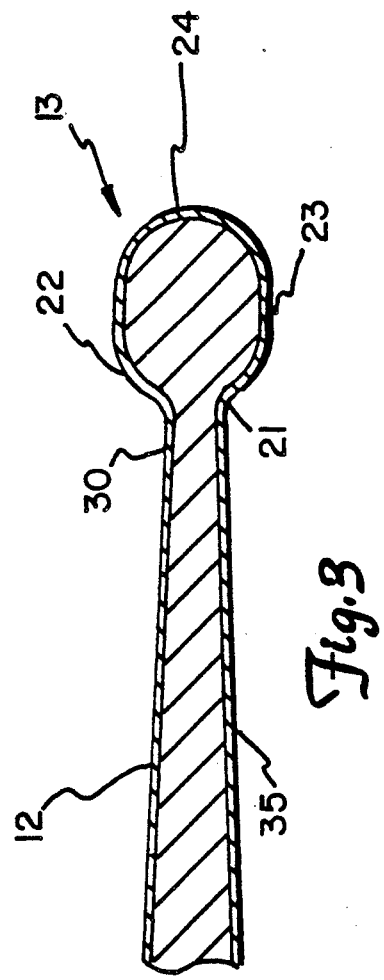
FIG. 3 is an enlarged cross sectional view of the end portion of a modified embodiment of a guide of the invention.

The guide shown in FIG. 1 includes a center portion 11 of substantially uniform diameter and a linearly tapered portion 12 at each end of the center portion 11. The tapered portions have a diameter which is gradually attenuated in a direction away from the center portion, and terminate in beads 13. Referring to FIGS. 2 and 3, a filet 21 is provided at the transition area between the tapered portion 12 and the bead 13 to reduce stress concentration at this point. The bead presents a generally rounded front end 24, which is preferably spherical in shape, the bead having a cylindrical portion 23 of a diameter substantially equal to or slightly more or less than the outer diameter of the center portion 11, and a generally rearwardly facing annular shoulder 22. The shoulder 22 may be gently rounded as shown in FIGS. 2 and 3, may be generally spherical, or may taper rearwardly more gently to merge into the filet 21. The rounded, forwardly facing portion of the bead serves to gently contact the interior of a blood vessel through which the guide is threaded to thus reduce damage to the lumen of the vessel.

In the embodiment shown in FIG. 3, the forward portion of the guide may include a cylindrical portion of uniform diameter 30 disposed between the tapered portion and the bead. It will be understood that the guides of the invention have substantially identical end portions which may be pre-bent; they desirably are substantially symmetrical about their axes and also with respect to a plane passing normal to such axes midway along the lengths of the guides.

Although the guide of the invention may be used for introduction of medical instruments such as catheters in any patient, it has particular advantages in the area of pediatrics, especially for the purpose of placing a catheter near the point at which the guide enters the vessel for intravenous fluid supply. For pediatric applications, the center portion 11 typically has a diameter of about 0.1 to about 0.4 mm, preferably about 0.25 mm, with a length in the range of about 8 cm to about 30 cm. The tapered portions 12 each have a uniformly decreasing diameter which ranges from the diameter of the center portion (eg., about 0.25 mm) to a diameter of about 0.05 mm to about 0.15 mm and preferably about 0.1 mm at the area adjacent the bead 13, the tapered portions having lengths of from about 1.5 cm to about 8 cm, with lengths of about 2 cm being preferred. The bead has a maximum diameter that is preferably substantially equal to that of the center portion, i.e., 0.1 mm to 0.4 mm, preferably about 0.25 mm. Thus, a guide wire of small diameter is provided and can be readily used in the small blood vessels of an infant. However, it is to be understood that these dimensions can be substantially increased to yield a device according to this invention for use with adults.

The wire employed in guides of the invention is made of a shape memory alloy which exhibits superelastic/pseudoelastic shape recovery characteristics. Such alloys are known in the field, and are characterized by their ability, within certain temperature ranges, to be deformed from an austenitic crystal structure to a stress-induced martensitic (SIM) structure, returning elastically to the austenitic shape when stress is removed. The alternate crystal structures provide the alloy with superelastic or pseudoelastic properties. Alternatively, a cold-worked martensitic microstructure can be used to provide enhanced shape recovery and a lower stiffness than, for example, stainless steel. Nitinol, an alloy of nickel and titanium, is a particularly preferred shape memory alloy in that it is commercially available and has been studied somewhat more than other shape memory alloys. Also, nitinol can exhibit this austinite-SIM-austenite transformation at the temperature range in which this invention will be utilized, i.e. in the room temperature to body temperature range.

Shape memory alloys are particularly valuable because of their capacity to elastically recover almost completely an initial configuration. There is little plastic deformation, even at relatively high strains. In other words, shape memory alloys have the capacity to avoid taking a "set" when deformed. In this manner, the guide of the invention may be substantially straight when unstressed, may elastically deform as it passes through curved body channels, and yet will recover its straight configuration when stress is removed. Also, nitinol and other pseudoelastic alloys are considerably more flexible than many of the metals conventionally used in medical instruments, such as stainless steel. Thus, less force need be exerted against the interior walls of the vessels to deform the guide of the invention along the desired path through a blood vessel, thereby decreasing trauma to the lumen of the vessel.

Shape memory alloys in general, and nitinol in particular, can be soldered or brazed only with some difficulty and the joint that results is not of great strength. According to the present invention, the terminal plugs or buttons are formed integrally at the ends of a length of shape memory alloy wire by suitable machining techniques, centerless grinding being the preferred technique. Centerless grinding has the advantage of yielding thin wires of precisely controlled diameter. Also, shape memory alloys are difficult to machine by most conventional methods, but centerless grinding can be used to form fairly complex radially symmetrical shapes without undue difficulty. The formation of an integral bead at the end of the guide as is used in the instant invention avoids the necessity of welding or otherwise attaching the end of a safety wire carried within an external helical coil of a conventional guide to a bead or button, and the integral bead is therefore far more resistant to being pulled from the end of guide than if it were welded to the wire end. This feature is of particular importance when one considers the propensity of some welded materials to crack or fracture under substantial stress at the weldments.

This invention does not require nor utilize an external helical coil. As mentioned above, shape memory alloys such as nitinol exhibit elastic deformation with minimal plastic deformation over a wide range of strains and also are very flexible. Thus, guides of the invention, having uniformly decreasing diameters in their tapered portions, exhibit controlled flexibility at their tips.

Additionally, the lack of a wound wire coil results in a smoother external surface of the guide. The rougher surface of a helically wound coil has numerous disadvantages, including resistance to the advancement of a catheter over the guide wire and a propensity to snag on the distal end of a needle. Numerous workers have striven to minimize these effects by a variety of methods ranging from covering coils with plastic coatings which fill the troughs between the wires to micropolishing a coiled flat wire. Reference is made to e.g., U.S. Pat. Nos. 4,003,369, 3,973,556, 4,579,127 and 4,456,017. However, by forming the instant invention via centerless grinding as described above, a precisely machined guidewire is obtained with the desired flexibility and a substantially smooth surface.

As noted above, each tapered portion 12 tapers uniformly from a larger diameter at its intersection with the center portion 11 to a smaller diameter adjacent the bead 13. The center portion gives the guide the stiffness necessary to propagate it along the artery or vein, while the tapered portion provides greater flexibility at the tip so that the guide can be easily inserted and maneuvered. Furthermore, by providing a uniformly decreasing diameter, the flexibility accordingly increases uniformly toward the tip without any abrupt preferred bending areas. By avoiding relatively abrupt changes in the diameter of the wire, corresponding abrupt changes in the flexibility of the wire producing points along the wire with high flexural stress gradients are also avoided. If a guide with abrupt diameter changes is subjected to repeated flexion, structural degradation and possibly a break in the wire at these areas of abrupt diameter change may be induced. However, by providing a uniformly decreasing diameter, this difficulty is avoided because there are no such localized areas of preferred bending. Also, the use of a circular cross section rather than a flat wire of decreasing thickness provides the same degree of flexibility in any direction so the surgeon does not have to inspect the wire before inserting it or turn it inside the patient until the wire is properly aligned.

The guide wire depicted in FIG. 1 is symmetrical about its mid-point. This double ended design makes the guide wire easier and safer to use. With a small diameter wire such as is used in pediatric care, it is difficult to rapidly discern with the unaided eye which end has the taper and should be inserted into the hollow introducing needle. The double ended construction eliminates the need to waste valuable time in surgery trying to find the proper end. This also enhances safety by preventing the inadvertent use of the "wrong" end which in non symmetrical guides may be relatively inflexible and may cause trauma to a patient's tissues as shown in FIG. 3, a thin coating (35) may also be applied to the instant invention for various purposes. For example, PTFE may be used to reduce friction between the guide and the catheter, an anticoagulant may be applied to enhance thromboresistance (resistance to blood clotting), or a radiopaque material can be utilized to enhance visualization by the application of x-rays, if so desired. These coatings do not have any significant structural effects, however, and they may be used without changing the physical nature or operation of the invention.

While preferred embodiments of the present invention have been described, it should be understood that various changes, adaptations and modifications may be made therein without departing from the spirit of the invention and the scope of the appended claims.

What is claimed is:

1. A guide useful for guiding a catheter within a blood vessel, comprising an elongated, flexible metal wire of shape memory alloy having a central portion of uniform diameter and identical tapered end portions of continuously decreasing diameter each terminating in an integral, enlarged diameter bead, the guide wire being formed from a single length of shape memory alloy wire having a uniform diameter by the process of centerless grinding, the ends of the wire being characterized by smooth, rounded transition between the ends of the tapered portions and the respective beads.

2. The guide of claim 1 further comprising a thin coating covering the external surface of said wire.

3. The guide of claim 1 in which the cross section of the guide at any point along its length is circular and in which the diameter of the bead is substantially equal to the diameter of the central portion.

4. The guide of claim 3 in which the diameter of the central portion and of the bead is not greater than about 0.4 mm, and wherein the smallest diameter of the tapered portion is not greater than about 0.15 mm.

5. The guide wire of claim 4 in which the tapered end portions have lengths in the range of about 1.5 cm to about 8 cm.

* * * * *